US008424362B2

(12) United States Patent
Hajishah et al.

(10) Patent No.: US 8,424,362 B2
(45) Date of Patent: Apr. 23, 2013

(54) METHODS AND APPARATUS FOR CALIBRATING A VACUUM COMPONENT OF A PHACOEMULSIFICATION SYSTEM

(75) Inventors: Abraham Hajishah, Irvine, CA (US);
David A. King, Pleasanton, CA (US);
Michael J. Claus, Newport Coast, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 612 days.

(21) Appl. No.: 12/632,938

(22) Filed: Dec. 8, 2009

(65) Prior Publication Data
US 2010/0107723 A1  May 6, 2010

Related U.S. Application Data

(63) Continuation-in-part of application No. 11/558,432, filed on Nov. 9, 2006, now Pat. No. 7,628,054.

(51) Int. Cl.
*G01L 27/00* (2006.01)
(52) U.S. Cl.
USPC ................ 73/1.58; 73/1.25; 73/1.26; 73/1.57
(58) Field of Classification Search .................... 73/1.01, 73/1.25, 1.26, 1.57, 1.58
See application file for complete search history.

(56) References Cited

U.S. PATENT DOCUMENTS

| 4,873,655 | A | | 10/1989 | Kondraske |
|---|---|---|---|---|
| 5,808,175 | A | | 9/1998 | Chang |
| 5,830,176 | A | * | 11/1998 | Mackool ........................ 604/22 |
| 5,876,016 | A | * | 3/1999 | Urban et al. .................. 248/159 |
| 5,938,677 | A | * | 8/1999 | Boukhny et al. ............... 606/169 |
| 6,283,937 | B1 | * | 9/2001 | Takamatsu et al. ............. 604/31 |
| 6,644,092 | B1 | | 11/2003 | Oppel |
| 6,780,166 | B2 | * | 8/2004 | Kanda et al. ..................... 604/31 |
| 6,802,209 | B2 | | 10/2004 | Joos et al. |
| 7,086,272 | B2 | | 8/2006 | Wu et al. |
| 7,216,048 | B2 | | 5/2007 | Wang et al. |
| 7,785,316 | B2 | * | 8/2010 | Claus et al. .................... 604/521 |
| 7,914,482 | B2 | * | 3/2011 | Urich et al. ..................... 604/65 |
| 8,092,427 | B2 | * | 1/2012 | Urich et al. ................... 604/118 |
| 2001/0023331 | A1 | * | 9/2001 | Kanda et al. .................... 604/43 |
| 2004/0074282 | A1 | | 4/2004 | Morgan et al. |
| 2005/0245886 | A1 | * | 11/2005 | Devine et al. ................. 604/264 |

(Continued)

FOREIGN PATENT DOCUMENTS

| CH | 692637 A5 | 8/2002 |
|---|---|---|
| EP | 0316763 A1 | 5/1989 |
| GB | 2372331 A | 1/2001 |
| KR | 2001037428 A | 5/2001 |

*Primary Examiner* — David Rogers
(74) *Attorney, Agent, or Firm* — Abbott Medical Optics Inc.

(57) ABSTRACT

Methods and apparatuses are provided for calibrating a vacuum component of a phacoemulsification system at different elevations. The design comprises running a vacuum component to be calibrated at an elevation; determining a maximum vacuum pressure available at the elevation; determining a range of vacuum pressure available from running the vacuum component at the elevation; calibrating the vacuum component based at least in part on a the maximum vacuum pressure available and the range of vacuum pressure available. The design also comprises a to be calibrated vacuum component; a pressure delivery device; an altimeter configured to determine the elevation of the vacuum component; component reading hardware configured to read at least one measured value from the pressure sensing components of the vacuum component when exposed to at least one pressure value from the pressure delivery device; and a computer configured to correlate a plurality of measured values to the elevation.

17 Claims, 8 Drawing Sheets

U.S. PATENT DOCUMENTS

2006/0100807 A1     5/2006   Koukol et al.
2007/0010730 A1*   1/2007   Gordon ......................... 600/398
2008/0139994 A1*   6/2008   Mackool et al. ................ 604/22
2009/0299672 A1    12/2009   Zhang et al.

* cited by examiner

METHODS AND APPARATUS FOR CALIBRATING A VACUUM COMPONENT OF A PHACOEMULSIFICATION SYSTEM

This application claims priority to and is a continuation-in-part of U.S. Ser. No. 11/558,432 filed on Nov. 9, 2006, the entirety of which is hereby incorporated by reference.

BACKGROUND OF THE INVENTION

1. Field of the Invention

The present invention relates generally to the field of digital measurement systems, and more specifically to a calibration utility used to calibrate analog signals obtained from a sensor in a non-linear measurement system.

2. Description of the Related Art

Today's safety critical systems, such as medical products or surgical equipment, require highly accurate measurement of vacuum and pressure to ensure proper instrument control and safe use in an operating theater. In a medical environment, a precision surgical device, such as a phacoemulsification machine, typically includes a pressure sensor that converts detected pressure into a representative or proportional physical motion to control said pressure. The machine measures the resultant analog or continuous signal produced due to this physical motion and converts the signal produced into a digital representation. This digital representation or signal can be transmitted to the machine's system processor and used to display the measured pressure values in human readable units (e.g. mmHg).

Current safety critical system designs can hinder system performance and ultimately cause harm to the patient in that the relationship between the detected physical pressures or sensor component motions read or encountered by the sensor and the corresponding actual values may differ by an unquantifiable amount, or their relationship may be non-linear. For example, the measurement system may measure an analog signal of 1000 units of motion from the pressure sensor that represents an actual pressure of 100 mmHg. The system may measure an analog signal of 500 units of pressure or motion from the same pressure sensor that represents an actual pressure of approximately 30 mmHg, more or less, making correlating movement to pressure difficult and inexact. Further, the system may exhibit non-linear effects where the extent of the resultant non-linear output may vary over different segments of the measurement range of the pressure sensor. In this situation, the system may generate analog signals that are, for example, very close to being linear at one end of the measurement range and less linear at the other end of the systems measurement range. The amount or actual extent of the systems non-linearity found in current designs depends upon numerous factors including the sensor mechanism used to convert pressure, or another parameter such as altitude, speed, time, or volume, to motion, the motion measurement system employed, and the method used to convert the analog measurement into a digital representation or signal.

A major commercial problem with regard to current designs is that such designs rely on a manual procedure to calibrate the system. For example, to calibrate a typical phacoemulsification system, an operator connects a syringe or other manual pressure-generating device to provide a baseline pressure input. The operator generates a known amount of pressure and measures the output using the measurement system. Typically, two points are measured; one at the low end and the other at the high end of the system's measuring range. The operator assumes the measurement system to be linear across the range of values between these two measured points. The operator then uses interpolation to derive addition values for any arbitrary measured value between these two measured points in order to determine the actual pressure. Such manual calibration techniques have many issues, not the least of which is the operator being required to generate a precise amount of pressure at two points along the system's measurement range. Generating a precise amount of pressure using a manual device is awkward for the operator and difficult to perform consistently and reliably, particularly at the extreme ends of the systems measurement range. Moreover, many of today's measurement systems are non-linear over a portion or the entire range of the measurement system and will not produce accurate measurements when calibrated using manual calibration techniques.

Thus, today's measurement system designers are faced with a difficult and complex implementation challenge to ensure accurate, consistent, and precise calibration of non-linear measurement systems to provide proper control and feedback of the surgical instrument, found in the phacoemulsification machine example, and the required level of safety in an operating theater or other safety critical environment.

Based on the foregoing, it would be advantageous to provide a measurement calibration utility for use in safety critical systems that overcomes the foregoing drawbacks present in previously known manual procedures used in the operation and calibration of measurement systems.

SUMMARY OF THE INVENTION

According to one aspect of the present design, there is provided a method for calibrating a vacuum component of a phacoemulsification system at an elevation, comprising supplying a vacuum component to be calibrated; running the vacuum component to be calibrated at the elevation; determining a maximum vacuum pressure available from running the vacuum component at the elevation; determining a range of vacuum pressure available from running the vacuum component at the elevation; calibrating the vacuum component based at least in part on the maximum vacuum pressure available and the range of vacuum pressure available.

According to another aspect of the present design, there is provided a method for calibrating a vacuum component of a phacoemulsification system to properly run at any elevation, comprising supplying a to be calibrated vacuum component; running the to be calibrated vacuum component; determining a maximum vacuum pressure available from running the to be calibrated vacuum component; determining a range of vacuum pressure available from running the to be calibrated vacuum component; providing known degradation specifications of the vacuum component at various elevation changes; determining the elevation of the vacuum component to be calibrated; and calibrating the vacuum component based at least in part on the maximum vacuum pressure available, the range of vacuum pressure available, and the known degradation specifications of the vacuum component at the determined elevation.

According to another aspect of the present design, there is provided an apparatus for calibrating a vacuum component of a phacoemulsification system at an elevation, comprising a to be calibrated vacuum component comprising pressure sensing components; a pressure delivery device configured to deliver pressure to the vacuum component; an altimeter configured to determine the elevation of the vacuum component; component reading hardware configured to read at least one measured value from the pressure sensing components of the vacuum component when exposed to at least one pressure value from the pressure delivery device; and a computer configured to correlate a plurality of measured values to the elevation.

According to one aspect of the present design, there is provided a method for calibrating an analog sensor used in a digital measurement system. The method comprises generating a precise pressure value set at multiple calibration points and supplying the precise pressure value set to a known good pressure sensor and an uncalibrated pressure sensor, detecting sensor changes for the known good pressure sensor and the uncalibrated pressure sensor based on each precise pressure value generated, polling an actual pressure reading associated with a sensor change for the known good pressure sensor and the uncalibrated pressure sensor for each calibration point, and establishing a mathematical relationship between measured value readings and actual pressure for the uncalibrated sensor, wherein the establishing converts the uncalibrated sensor to a newly calibrated sensor.

According to another aspect of the present design, there is provided an apparatus for calibrating a sensor. The apparatus comprises an uncalibrated sensor comprising pressure sensing components, a pressure delivery device configured to deliver precise pressure values to the uncalibrated sensor, component reading hardware configured to read at least one measured value from the pressure sensing components of the uncalibrated sensor when exposed to at least one precise pressure value from the pressure delivery device, and a computational device configured to correlate a plurality of measured values to precise pressure values and establish a relationship between measured values and precise pressure values.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE INVENTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to managing an accurate, reliable, and efficient means to calibrate a wide variety of measurement systems in a safety critical system. However, the present design is not limited to a pressure measurement systems implementation, and may provide a calibration utility or mechanism for use in any kind of measurement system that involves a non-linear measurement of an analog or continuous value by a digital system. Examples may include, but are not limited to, calibration of systems that measure light intensity, altitude, voltage, speed, time, and vacuum.

While the present design may be used in various environments and applications, it will be discussed herein with a particular emphasis on a medical or hospital environment, where a surgeon or health care practitioner performs. For example, one embodiment of the present design is a phacoemulsification surgical system that comprises an independent graphical user interface (GUI) module, an instrument host module, and a controller module, such as a foot switch, to control the surgical system.

The present design provides a system and method for a calibration mechanism that may be used to precisely calibrate a pressure measurement system over its entire operational range. This system and method may enable accurate and precise measurements to be made at all points along the detectable range of pressure values reported by a pressure sensor connected to the pressure measurement system. The system and method may provide a quick, easy to use, and reliable mechanism flexible enough to allow the calibration of a wide variety of systems, including but not limited to pressure measurement systems.

While the present design may be employed in a variety of systems, it is illustrated herein in an exemplary phacoemulsification system. It is to be understood that any type of system having pressure calibration issues, or more specifically pressure sensor reading calibration issues, may benefit from the design presented herein, and such a design is not limited to a phacoemulsification system or even a medical system. The present design may be implemented in, for example, systems including but not limited to phacoemulsification-vitrectomy systems, vitrectomy systems, dental systems, heart-lung surgical devices, and industrial applications such as HVAC (heating, ventilation, and air conditioning) systems, oil and gas systems, metrology devices, and aerospace applications.

System Example

Figure 1:
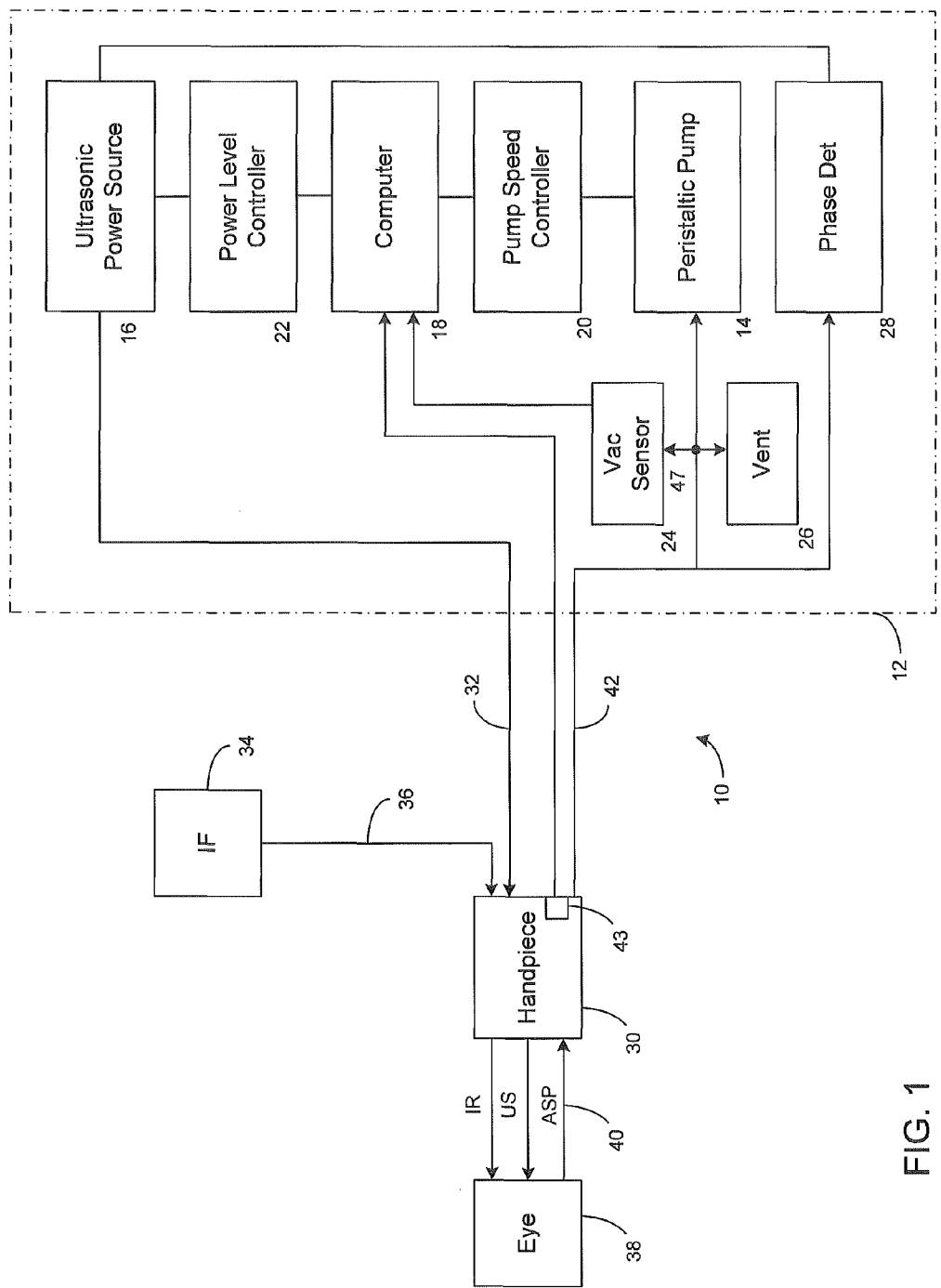
FIG. 1 is a functional block diagram of a phacoemulsification system that may be employed in accordance with an aspect of the present invention.

FIG. 1 illustrates an example of a phacoemulsification system that may employ the present design. FIG. 1 illustrates the system and pertinent components in block diagram form, indicated generally by the reference numeral 10. The system has a control unit 12, indicated by the dashed lines in FIG. 1 which includes a variable speed peristaltic pump 14, which provides a vacuum source, a source of pulsed ultrasonic power 16, and a microprocessor computer or computational device 18 that provides control outputs to pump speed controller 20 and ultrasonic power level controller 22. A vacuum sensor 24 provides an input to computer 18 representing the vacuum level on the input side of peristaltic pump 14. Suitable venting is provided by vent 26.

A phase detector 28 provides an input to computer 18 representing a phase shift between a sine wave representation of the voltage applied to a handpiece/needle 30 and the resultant current into the handpiece 30. The block representation of the handpiece 30 includes a needle and electrical means, typically a piezoelectric crystal, for ultrasonically vibrating the needle. The control unit 12 supplies power on line 32 to a phacoemulsification handpiece/needle 30. An irrigation fluid source 34 is fluidly coupled to handpiece/needle 30 through line 36. The irrigation fluid and ultrasonic power are applied by handpiece/needle 30 to a patient's eye, or affected area or region, indicated diagrammatically by block 38. Alternatively, the irrigation source may be routed to the eye 38 through a separate pathway independent of the handpiece. The eye 38 is aspirated by the control unit peristaltic pump 14 through line/handpiece needle 40 and line 42. A switch 43 disposed on the handpiece 30 may be utilized as a means for enabling a surgeon/operator to select an amplitude of electrical pulses to the handpiece via the computer 18, power level controller 22 and ultrasonic power source 16 as discussed herein. Any suitable input means, such as, for example, a foot pedal (not shown) may be utilized in lieu of the switch 43.

Figure 2:
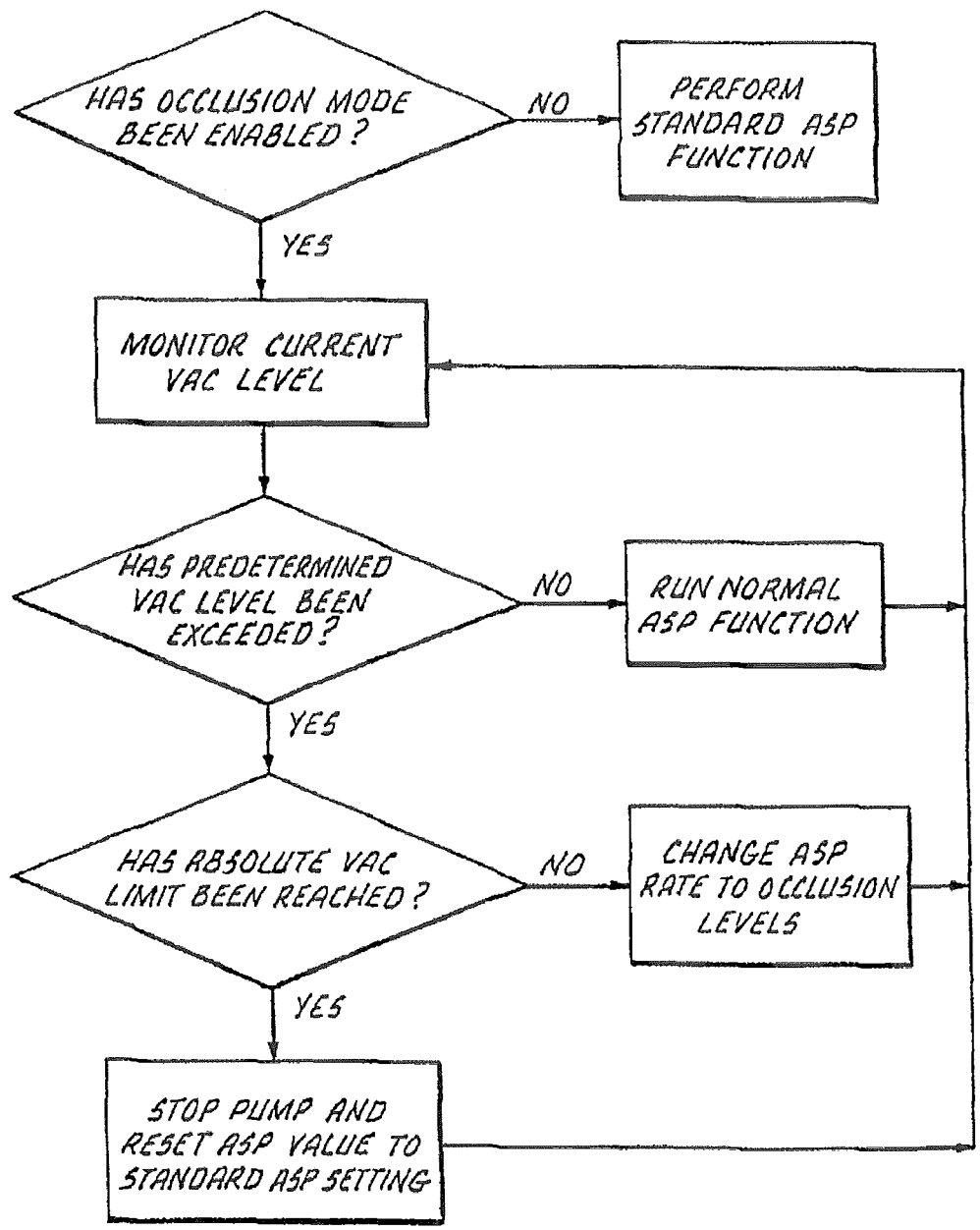
FIG. 2 is a flow chart illustrating the operation of the occluded-unoccluded mode of the phacoemulsification system with variable aspiration rates.
Figure 3:
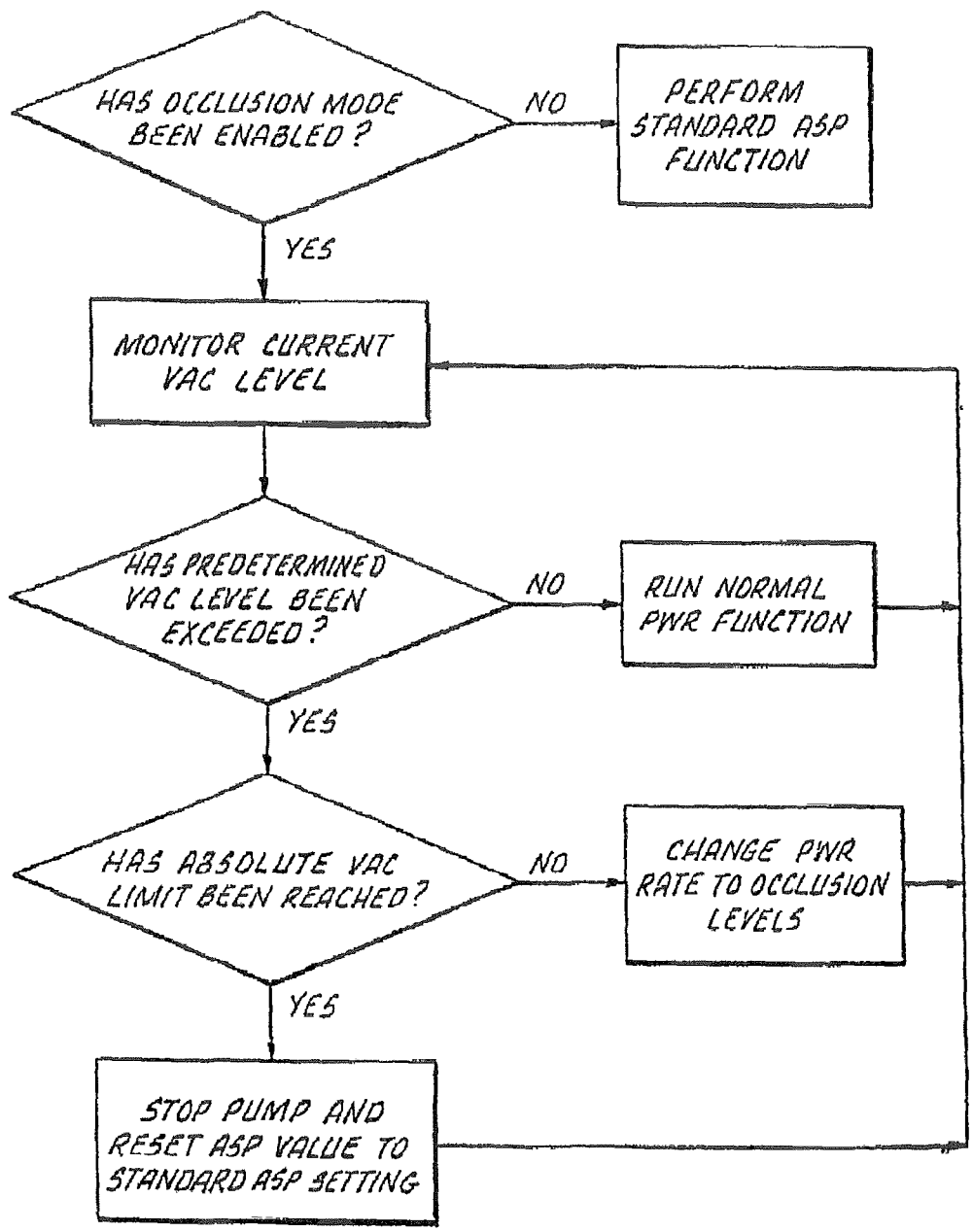
FIG. 3 is a flow chart illustrating the operation of the occluded-unoccluded mode of the phacoemulsification system with variable ultrasonic power levels.

The computer 18 may be any type of computational device able to provide the functionality disclosed herein. Computer 18 responds to preset vacuum levels in input line 47 to peristaltic pump 14 by means of signals from the previously mentioned vacuum sensor 24. Operation of the control unit in response to the occluded-unoccluded condition of handpiece 30 is shown in the flow diagram of FIG. 2. FIGS. 2 and 3 show that pressures are employed in the system in a variety of contexts and accurate pressure and/or vacuum readings are important in the proper operation of a system such as a phacoemulsification system, vitrectomy system, and/or combined phacoemulsification/vitrectomy system.

As shown in FIG. 2, if the handpiece aspiration line 40 becomes occluded, the vacuum level sensed by vacuum sensor 24 may increase. The computer 18 may provide operator-settable limits for aspiration rates, vacuum levels and ultrasonic power levels. As illustrated in FIG. 3, when the vacuum level sensed by vacuum sensor 24 reaches a predetermined level as a result of occlusion of the handpiece aspiration line 40, computer 18 provides signals to pump speed controller 20 to change the speed of the peristaltic pump 14 which, in turn, changes the aspiration rate. Depending upon the characteristics of the material occluding handpiece/needle 30, the speed of the peristaltic pump 14 can either be increased or decreased. When the occluding material is broken up, the vacuum sensor 24 registers a drop in vacuum level, causing computer 18 to change the speed of peristaltic pump 14 to an unoccluded operating speed.

In addition to changing the phacoemulsification parameter of aspiration rate by varying the speed of the peristaltic pump 14, the power level of the ultrasonic power source 16 can be varied as a function of the occluded or unoccluded condition of handpiece 30. FIG. 3 illustrates in flow diagram form a basic form of control of the ultrasonic power source power level using computer 18 and power level controller 22. The flow diagram of FIG. 3 corresponds to the flow diagram of FIG. 2 but varies the phacoemulsification parameter of the ultrasonic power level.

As may be appreciated from FIGS. 1-3, pressure/vacuum readings are of particular importance and affect several of the components illustrated in FIG. 1. Highly accurate pressure/vacuum values provide clear benefits for the performance of the system 10, and poorly calibrated or inaccurate pressure readings, values, or information can materially degrade performance in such a system.

Calibration

Figure 4:
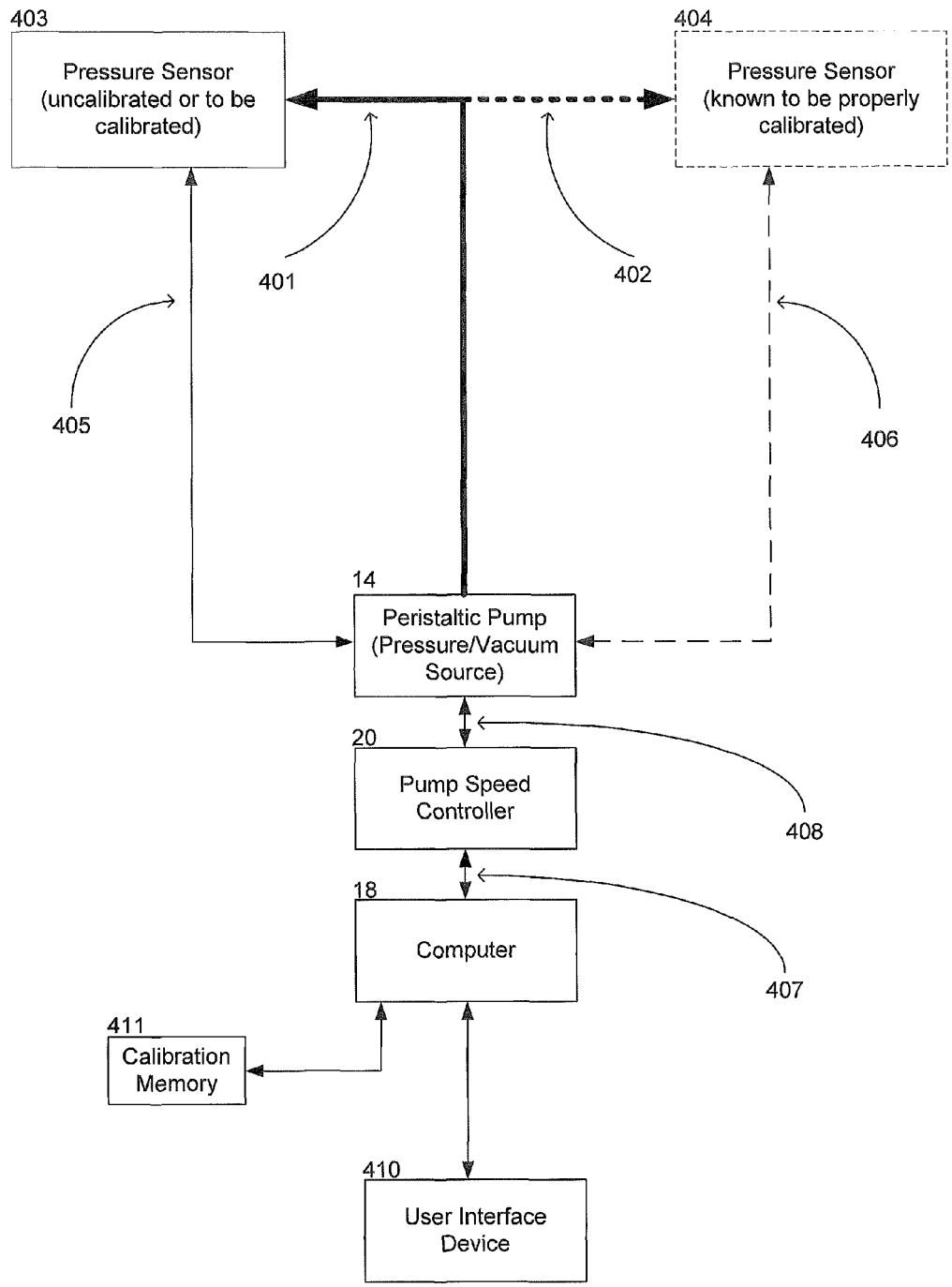
FIG. 4 illustrates the calibration system components and interfaces in accordance with the present design.

FIG. 4 illustrates a functional block diagram of a calibration system setup in an arrangement that includes the components and interfaces of an automated mechanism that provides multiple calibration points across the entire range of the measurement system in accordance with the present design. This arrangement may use the pressure/vacuum generation equipment configured within a system such as the phacoemulsification system 10 to generate pressure and may automatically read the actual pressure for each point using a known, good pressure sensor. This calibration system may allow the operator/user an optional means to enter the actual pressure reading for each calibration point manually. The calibration system may include a peristaltic pump 14 or other pressure generating device configured to generate pressure and/or vacuum. A connection line 401 from the peristaltic pump 14 may supply pressure to a pressure sensor 403, or an uncalibrated sensor, that is ready for calibration. A second connection line 402 from the peristaltic pump 14 may supply pressure to a properly calibrated pressure sensor 404, where use of the properly calibrated pressure sensor 404 is optional.

The calibration system may be configured to provide electrical connections from both pressure sensors to a computer 18, i.e. processor or other computational device, for providing control and signaling at line 405 for the "to be calibrated" pressure sensor 403 and at line 406 for the properly calibrated, or known, pressure sensor 404. A control connection 407 from computer 18 may connect a pump speed controller 20 configured to manage the peristaltic pump 14 through an electrical connection 408. The electrical connections between the computer 18 and pump 14, and between pump 14 and pump speed controller 20, and between user interface device 410 and pressure sensors at 403 and 404 may be realized using a communications network, for example wired via RS-232 connections or a wireless connection supported by Bluetooth™, or any other suitable means for passing control and data signals between devices or components.

A user interface device 410, for example a graphical user interface host system, may be connected to computer 18 to provide operational control for the calibration system. The user interface device 410 may include but is not limited to a touch screen monitor, mouse, keypad, foot pedal switch, and/or a computer monitor. The computer 18 may include a calibration memory 411 that may be configured to store, and subsequently retrieve, data obtained during the calibration process. The calibration memory may be resident within the computer 18 or realized using external devices and/or software.

The present design may retrieve and manipulate the captured pressure/vacuum data using various mathematical functions, methods, and operations. In particular, the calibration system may use interpolation to create additional data points from the stored data read from the formerly uncalibrated and newly calibrated pressure sensor in calibration memory 511. Computer 18 may employ techniques such as averaging, weighted averaging, rounding, truncation, cubic spline mapping, curve fitting, or other mathematical techniques with the goal of matching or correlating pressure or vacuum sensed values or parameters over a particular range to accurate pressure representations over a selected range, such as the range of operating pressures or the physical variations expected in the sensor, such as the distance a mechanical element within the sensor may be altered. The computer or computational device 18 may convert a linear displacement of a mechanical device or sensor component as measured in millimeters or degrees to a pressure/vacuum reading such as inches of Mercury or pounds per square inch (psi).

Prior to operation of the calibration system, the operator/user may specify the number of calibration points to be measured during the calibration procedure and the entire measurement range, i.e. endpoints, as parameters over which the calibration is to be performed using the user interface device 410. Once the parameters are entered, the computer or computational device 18 may then direct the pressure/vacuum source, such as peristaltic pump 14 via the pump speed controller 20, to automatically produce the requested number of pressure values. At each pressure value, the computer or computational device 18 may interrogate the known good pressure sensor 404 to obtain and store the actual pressure values for each calibration point. In addition, the computer 18 may interrogate the "to be calibrated" pressure sensor 403 to obtain and store the actual measured pressure values exhibited for each calibration point. The relationship between the known good values and the actual measured values may then be stored in the calibration memory 411.

Alternately, a given number of points may be evaluated without operator intervention or designation of a specific point quantity or operating range. The computer may have a general operating range, such as 20 to 400 psi, and may divide this range into a known set of ranges, such as 20, 80, 140, 170, 200, 215, 230, 260, 320, and 380 psi (seven readings, with increased readings in a range where operation is known to frequently occur, and/or within ranges where the pressure sensor is known or suspected to have nonlinearities). Additional readings may of course be provided or increased or decreased depending on circumstances (multiple nonlinear regions, known linear performance over large regions, etc.). The system may then apply known values to a region or chamber or vessel containing the pressure sensor and take discrete measurements of some attribute of the pressure sensor, such as movement or deflection in millimeters or degrees. The physical movement is then tracked and maintained in, for example, calibration memory 411, and operated on using the computer 18 or a computational device.

Figure 5:
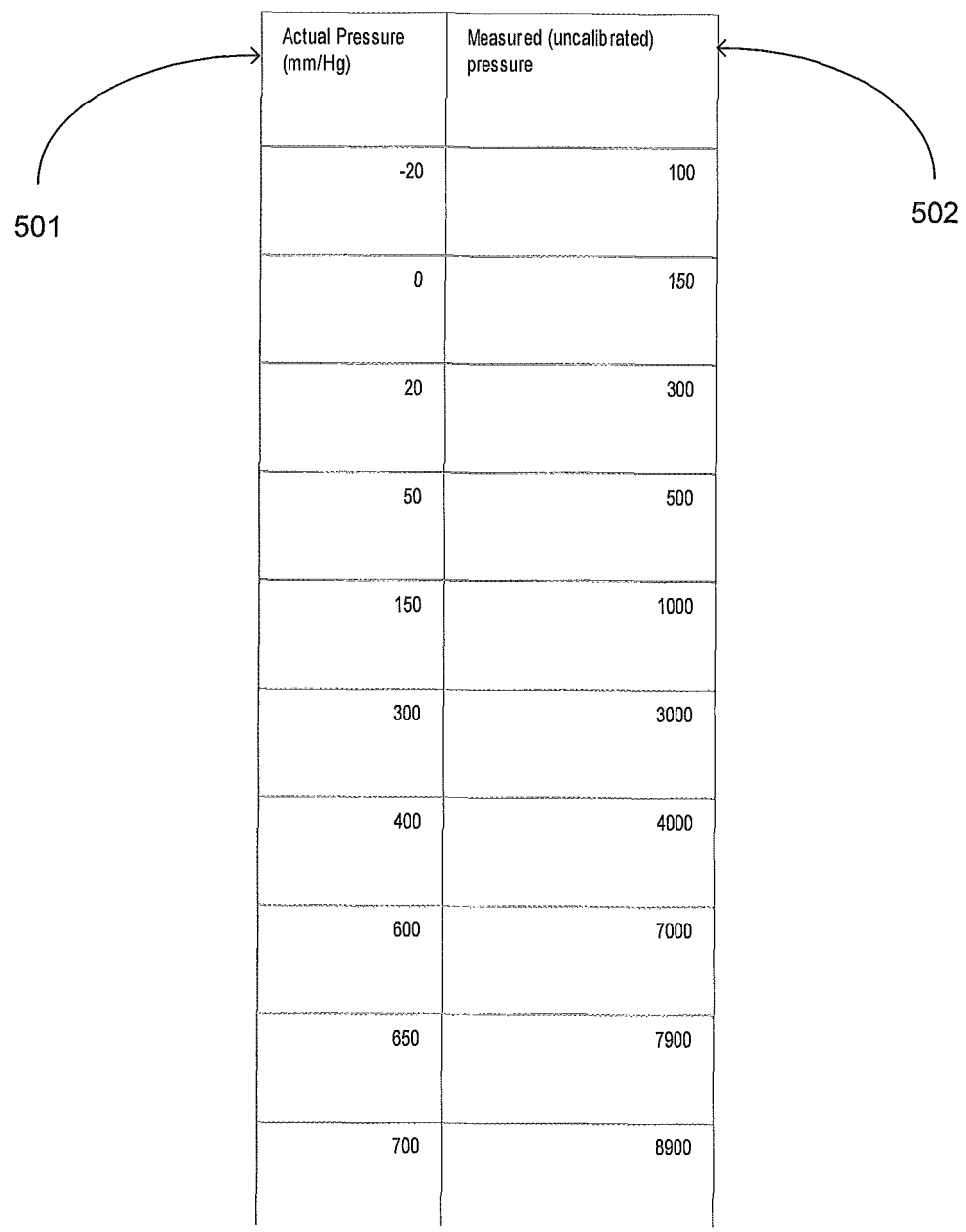
FIG. 5 shows an example of data that may be collected by the calibration system from each pressure sensor to obtain the actual pressure values and the measured values for each calibration point in accordance with the present design.

FIG. 5 illustrates an example of data that may be collected by the calibration system from each pressure sensor to obtain the actual pressure values 501 and the measured or uncalibrated values 502 for each calibration point in accordance with the present design. In this set of example data, the actual pressure from a known good sensor and the measured or uncalibrated measured pressure from the "to be calibrated" sensor may be related in a non-linear manner.

Figure 6:
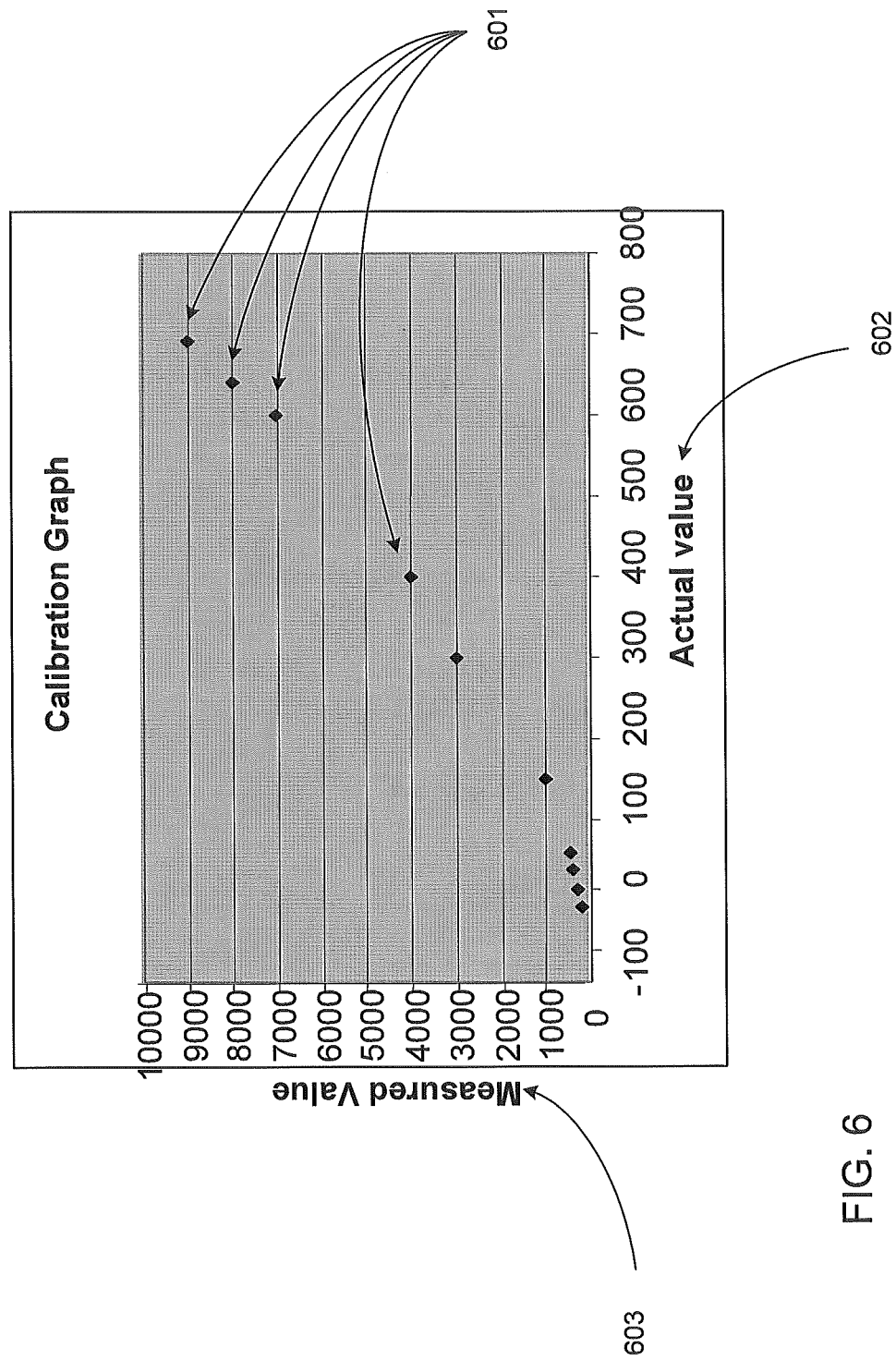
FIG. 6 is a calibration graph using the example data plotted to show the non-linear relationship between the measured and actual data values in accordance with the present design.

FIG. 6 illustrates a calibration graph using the example data at 601 from FIG. 5 plotted to show the non-linear relationship between the measured value 603 and measured values 602 in accordance with the present design. Once the calibration data is collected and data values stored in the calibration memory, if desired, the stored data may be retrieved and used by the present design to calculate the actual data value associated with any measured value read from the system's uncalibrated pressure sensor 403. For example, if the system reads a measured data value of 6000 from the uncalibrated pressure sensor 403, the present design may be configured to read the two calibration points immediately adjacent to this measure data value on a calibration curve. The calibration system may use the two adjacent calibration points to calculate the pressure value, or actual value, corresponding to this measured data value. In this example the adjacent calibration points used are 400 mmHg (associated with 4000 measured value) and 600 mmHg (associated with 7000 measured value). The present design may dynamically determine the actual pressure value associated with the uncalibrated pressure sensor reading by, for example, interpolating between the adjacent points to obtain:

$$(7000-6000)/(7000-4000)=(600-X)/(600-400) \quad (1)$$

Or in this case, X, representing actual pressure value, is equal to 533.33 mmHg.

Figure 7:
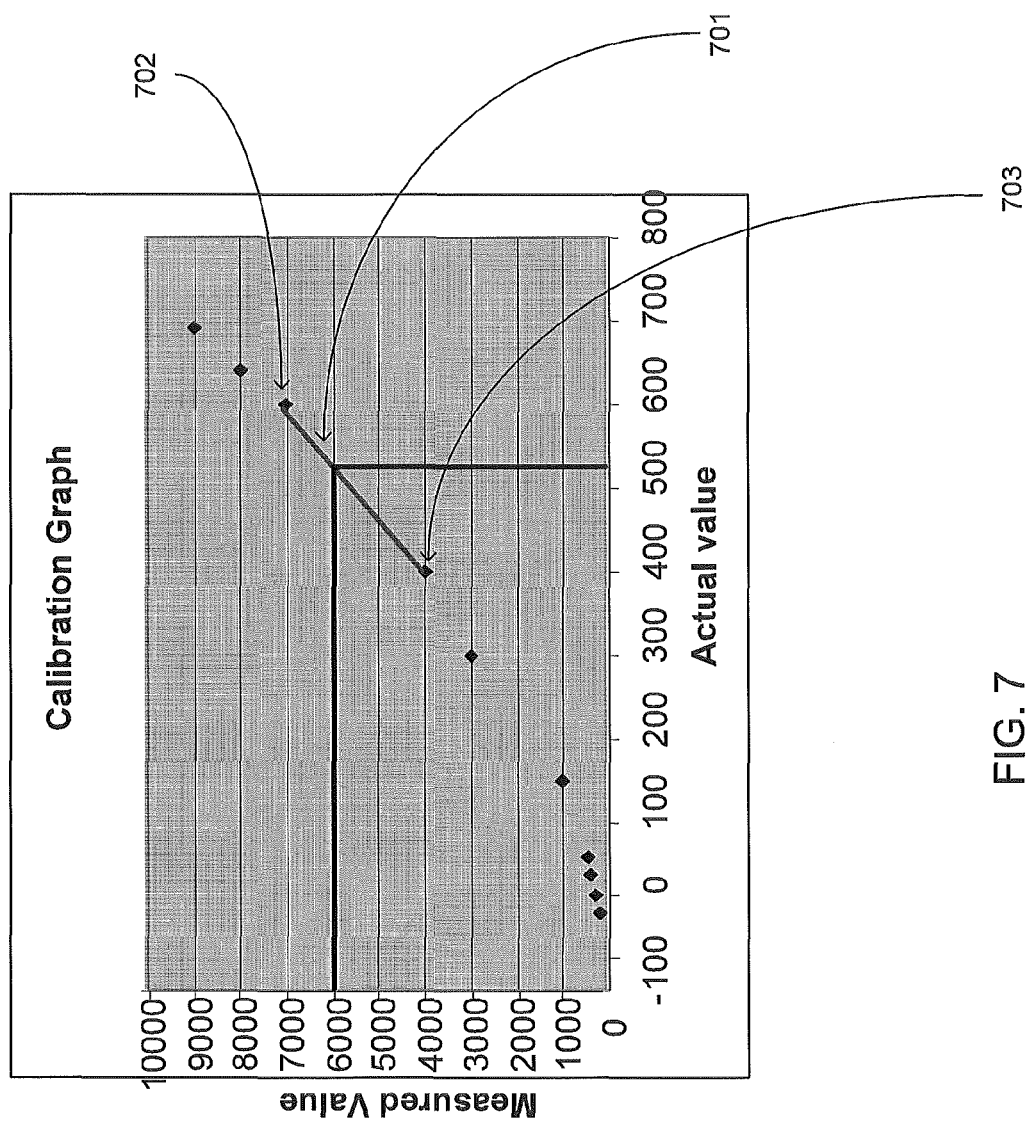
FIG. 7 illustrates how the slope from two adjacent calibration points is used to calculate the actual values using the example data in accordance with the present design.

FIG. 7 illustrates how the slope from two adjacent calibration points is used to calculate the actual values using the example data in accordance with the present design. In this example, the present design may define a line 701 that intersects the two adjacent calibration points at 702 and 703 respectively, used to calculate the slope of line 701. As noted, a measured value of 6000 from the uncalibrated pressure sensor 403 corresponds to an actual pressure of approximately 533.3 mmHg.

While FIGS. 6 and 7 illustrate a direct interpolation between points, as discussed above, other curves or mathematical relationships or representations may be generated based on the data obtained, such as cubic spline interpolation, or simply taking a value and extending it to the next value. For example, in the illustration of FIG. 6, the measured value of 3000 correlates with an actual value of 300, while the measured value of 4000 correlates with the actual value of 400. The lower or upper value may be maintained for the period between points, such as holding the 300 value for actual values between 300 and 400, or conversely holding the 400 value for actual values between 300 and 400, or even selecting an intermediate value such as 350 for all measured values between 3000 and 4000. Other schemes may be employed using the data obtained during the calibration procedure discussed herein.

Figure 8:
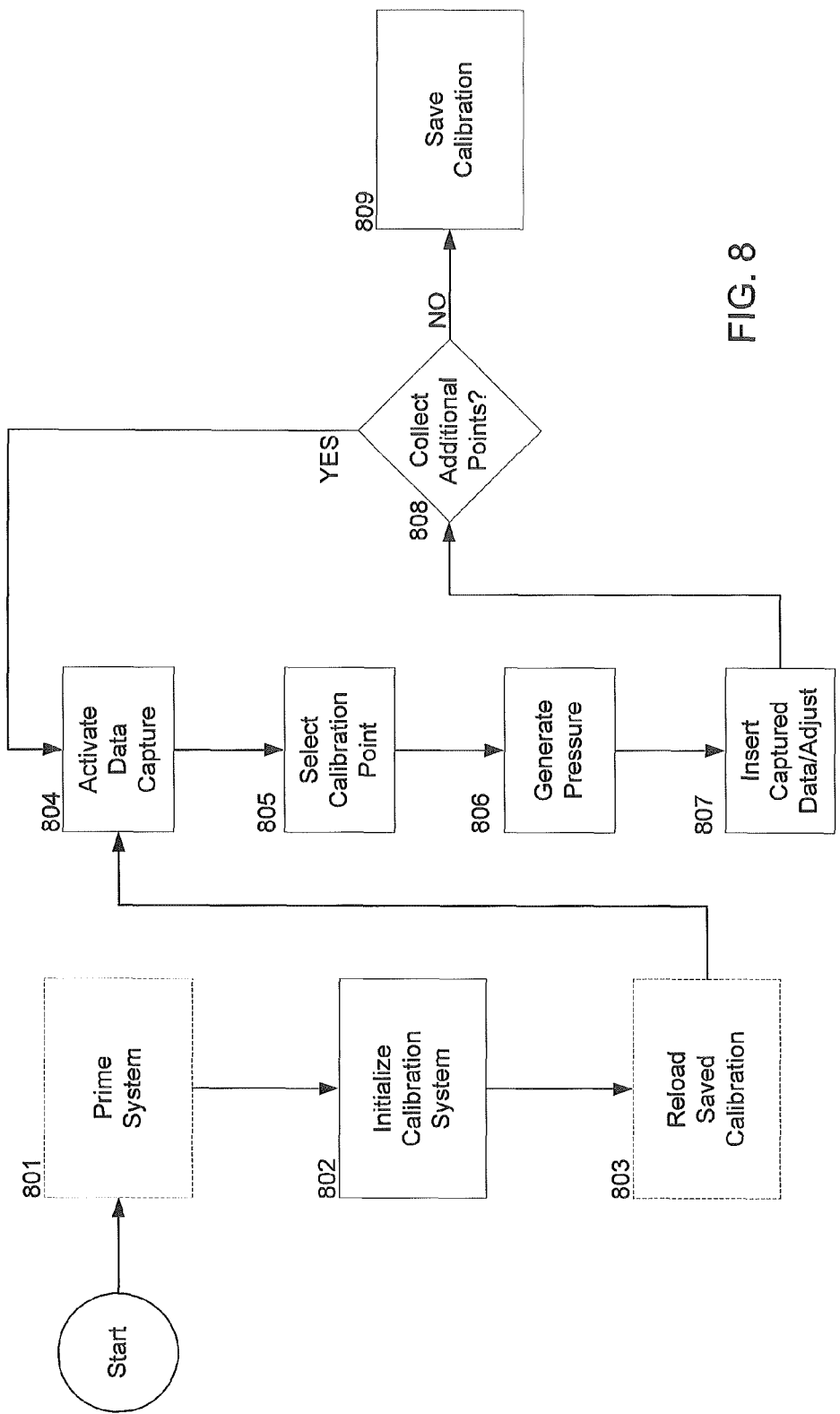
FIG. 8 is an example of operational activity flow that may be supported by the user interface device in accordance with an aspect of the present design.

FIG. 8 illustrates one example of operation of the user interface device 410 in accordance with the present design. The present design may provide a graphical user interface for use with such a calibration system. This particular embodiment may allow the user to calibrate a non-linear system using multiple calibration points, such as six calibration points. In this configuration, the operator/user may generate the required pressure for calibration using the mechanized system peristaltic pump 14, controlled by a foot pedal switch that is part of the phacoemulsification machine, or use the traditional manual syringe method. The operator/user may enter into the present design manually the known good actual values and the actual readings from the system to be calibrated, or allow the calibration utility to automatically enter the points and correct the measured pressure readings obtained from the "to-be-calibrated" pressure sensor 403 and enable correct readings to be collected from the pressure sensor 403. In order to obtain or collect six calibration points the operator/user may prime the phacoemulsification machine prior to calibration at 801, where priming comprises providing a pressure level or gas to a chamber or area within the device. Priming is optional, as the system may already be primed. The primed system may now be initialized at point 802, where initialization may take various forms, including but not limited to establishing connections between sensors and the computer, powering up the system or computer, establishing a set of calibration points, establishing a range of calibration points and a number of points, requesting specific user input, and so forth.

At point 803, the operator/user may instruct the machine to reload saved calibration data if available, and again this is optional. Reloading of existing calibration data is not mandatory to calibrate the system. Data capture is activated at point 804. During the data collection procedure, the operator may select at least one data point for calibration at 805. The operator/user may create a pressure at 806 using either a syringe or the foot pedal switch to operate the pump being the preferred embodiment. The present design internal pumps may provide a much more accurate and precise control mechanism for generating pressure than a manual syringe and thus reduce or eliminate any uncertainty associated with generating precise pressure values for use with the described calibration utility. In other words, the device may create pressure at point 806, typically a known pressure or vacuum level. At point 807, the data collection process may be suspended by the operator/user and the raw data captured by this process is inserted, or data captured may be automatically inserted. The operator/user or the system may also observe or poll or adjust a meter at point 207 if such adjustment is required. If available, another indicating device may be polled or tested and the device adjusted for the calibration point under consideration. The operator or system may repeat the data capture process at point 808, directing the system to loop back to activate data capture at point 804 and continue through point 807 until all calibration points are completed at point 808. The operator/user may complete the calibration process by saving the new calibration data at point 809 and optionally assigning a time stamp to the saved data.

The present design may be configured to enable the operator/user to enter the known good data values directly into the system using the user interface device 410. In this way, the present design does not need to interrogate the known good pressure sensor 404 directly by computer 18. Furthermore, the present design may collect and measure a variable number of calibration points and may vary the range, or encompass the full extent of the measurable range, over which the calibration utility operates, including varying the spread between each calibration point within the range under consideration. Arranged in this manner, the present design may reduce or eliminate the inaccuracy associated with current non-linear measurement systems.

The present design may be configured to automatically generate multiple calibration points across the range of the measurement system. In this configuration, the present design may employ the pressure generation equipment currently available in systems such as medical systems and the like and mechanize the reading the actual pressure for each calibration point from a known good pressure sensor.

Calibration at Various Elevations

An increase in elevation can affect how medical devices function. Typically, medical devices are manufactured and calibrated at or near sea level. Medical devices with systems requiring vacuum to operate a feature can be affected by an altitude change. For example, a phacoemulsification system with a vacuum component may not operate properly at higher altitudes. In order to accommodate operation of a phacoemulsification system at various altitudes it is necessary to properly calibrate the system. A phacoemulsification system may be calibrated by any method or combination thereof described herein. For example, according to an embodiment of the invention, a method of calibrating a vacuum component of a phacoemulsification system includes supplying a vacuum component to be calibrated, running the vacuum component at the location (elevation) where the system will be used, determining a maximum vacuum pressure and/or a range of vacuum pressure available from running the vacuum component at the elevation, and/or calibrating the vacuum component based at least in part on the maximum vacuum pressure available and/or the range of vacuum pressure available. The calibration methods disclosed herein help to determine the range and maximum vacuum pressure that the system can achieve. Based upon the vacuum pressure range, the maximum vacuum pressure, and/or the minimum vacuum pressure the phacoemulsification system may be adjusted to provide a maximum and minimum vacuum setting within the available vacuum range. Any other feature of the system may also be calibrated to the determined vacuum pressure range, including but not limited to the movement or displacement of the footpedal.

According to an embodiment, the methods described herein may further include generating a plurality of known pressures at multiple calibration points within a known operating range, wherein the known operating range is divided into a low range, a middle range, and a high range, wherein the middle range comprises intervals between the number of known pressures that are smaller than the intervals between the number of known pressures within the low range and the high range; and supplying the plurality of known pressures to the vacuum component to be calibrated to produce a plurality of measured pressure readings and the known pressures, wherein calibrating the vacuum component is also based on a mathematical relationship between the measured pressure readings and the known pressures. The generating step may also include employing an automated procedure establishing a plurality of calibration points across a measurement range applicable to the vacuum component.

The vacuum pressure range and maximum vacuum pressure may also be obtained in other ways. For example, they may be calculated based upon the altitude that the system is known to be running at. The calculation is based upon known specifications of the components of the system and their degradation of performance as the altitude increases.

According to an embodiment, a method of calibrating a vacuum component of a phacoemulsification system to properly run at any elevation includes supplying a to be calibrated vacuum component; running the to be calibrated vacuum component; determining a maximum vacuum pressure available from running the to be calibrated vacuum component; determining a range of vacuum pressure available from running the to be calibrated vacuum component; providing known degradation specifications of the vacuum component at various elevation changes; determining the elevation of the vacuum component to be calibrated; and calibrating the vacuum component based at least in part on the maximum vacuum pressures available, the range of vacuum pressure available, and/or the known degradation specifications of the vacuum component at the determined elevation. Running the to be calibrated vacuum component includes running the vacuum component to achieve the maximum and/or minimum vacuum pressure available at a particular elevation. Known degradation specifications of the vacuum component at various elevation changes may be any specifications known in the art for components used in systems that require vacuum pressure. As described herein, the vacuum component may comprise pressure sensing components, such as a pressure sensor.

The maximum vacuum setting may be determined by the available vacuum range and taking into consideration the overhead of the system. In one embodiment, the maximum vacuum setting is set at about 100 mmHg below the overhead for the vacuum regulator. This calculation gives the top end calibration for the system. This calibration provides accurate control and stability of the system for the user.

According to another embodiment, the system may also have an altimeter (internal or external to the system) so that the calibration could be adjusted dynamically as the altitude changes. According to an embodiment, an apparatus for calibrating a vacuum component of a phacoemulsification system at an elevation includes a to be calibrated vacuum component comprising pressure sensing components; a pressure delivery device configured to deliver pressure to the vacuum component; an altimeter configured to determine the elevation of the vacuum component; component reading hardware configured to read at least one measured value from the pressure sensing components of the vacuum component when exposed to at least one pressure value from the pressure delivery device; and a computer configured to correlate a plurality of measured values to the elevation determined by the altimeter.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A method for calibrating a vacuum component of a phacoemulsification system at an elevation, comprising:
    supplying a vacuum component to be calibrated;
    running the vacuum component to be calibrated at the elevation;
    determining a maximum vacuum pressure available from running the vacuum component at the elevation;
    determining a range of vacuum pressure available from running the vacuum component at the elevation;
    calibrating the vacuum component based at least in part on the maximum vacuum pressure available and the range of vacuum pressure available.

2. The method of claim 1, wherein the vacuum component comprises a pressure sensor.

3. The method of claim 1, wherein the range of vacuum pressure comprises a minimum vacuum pressure.

4. The method of claim 1, further comprising correlating the calibrated vacuum component comprising a calibrated range of vacuum pressure with displacement of a footpedal.

5. The method of claim 1, further comprising generating a plurality of known pressures at multiple calibration points within a known operating range, wherein the known operating range is divided into a low range, a middle range, and a high range, wherein the middle range comprises intervals between the number of known pressures that are smaller than the intervals between the number of known pressures within the low range and the high range; and supplying the plurality of known pressures to the vacuum component to be calibrated to produce a plurality of measured pressure readings and the known pressures, wherein calibrating the vacuum component is also based on a mathematical relationship between the measured pressure readings and the known pressures.

6. The method of claim 5, wherein generating comprises employing an automated procedure establishing a plurality of calibration points across a measurement range applicable to the vacuum component.

7. The method of claim 5, wherein generating comprises manually entering actual pressure readings for each of the measured pressures.

8. A method for calibrating a vacuum component of a phacoemulsification system to properly run at any elevation, comprising:
    supplying a to be calibrated vacuum component;
    running the to be calibrated vacuum component;
    determining a maximum vacuum pressure available from running the to be calibrated vacuum component;
    determining a range of vacuum pressure available from running the to be calibrated vacuum component;
    providing known degradation specifications of the vacuum component at various elevation changes;
    determining the elevation of the vacuum component to be calibrated; and
    calibrating the vacuum component based at least in part on the maximum vacuum pressure available, the range of vacuum pressure available, and the known degradation specifications of the vacuum component at the determined elevation.

9. The method of claim 8, wherein the vacuum component comprises a pressure sensor.

10. The method of claim 8, wherein the range of vacuum pressure comprises a minimum vacuum pressure.

11. The method of claim 8, further comprising correlating the calibrated vacuum component comprising a calibrated range of vacuum pressure with displacement of a footpedal.

12. An apparatus for calibrating a vacuum component of a phacoemulsification system at an elevation, comprising:
    a to be calibrated vacuum component comprising pressure sensing components;
    a pressure delivery device configured to deliver pressure to the vacuum component;
    an altimeter configured to determine the elevation of the vacuum component;
    component reading hardware configured to read at least one measured value from the pressure sensing components of the vacuum component when exposed to at least one pressure value from the pressure delivery device; and
    a computer configured to correlate a plurality of measured values to the elevation determined by the altimeter.

13. The apparatus of claim 12, wherein the vacuum component comprises a pressure sensor.

14. The apparatus of claim 12, further comprising calibration memory configured to store the correlation between the plurality of measured values and the elevation.

15. The apparatus of claim 12, wherein the vacuum component is connected to the computer using at least one selected from the group consisting of a wired connect and a wireless connection.

16. The apparatus of claim 12, wherein the pressure sensing components comprise mechanical elements configured to physically move to a certain position when exposed to a pressure.

17. The apparatus of claim 12, wherein the computer comprises a computational device.

* * * * *